(12) United States Patent
Wunsch, II et al.

(10) Patent No.: US 9,043,326 B2
(45) Date of Patent: May 26, 2015

(54) METHODS AND SYSTEMS FOR BICLUSTERING ALGORITHM

(75) Inventors: Donald Coolidge Wunsch, II, Rolla, MO (US); Rui Xu, Clifton Park, NY (US); Sejun Kim, Rolla, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 13/385,042

(22) Filed: Jan. 30, 2012

(65) Prior Publication Data

US 2012/0221573 A1    Aug. 30, 2012

Related U.S. Application Data

(60) Provisional application No. 61/462,121, filed on Jan. 28, 2011.

(51) Int. Cl.
    *G06F 17/30*      (2006.01)
    *G06F 19/24*      (2011.01)

(52) U.S. Cl.
    CPC .......... *G06F 17/30539* (2013.01); *G06F 19/24* (2013.01)

(58) Field of Classification Search
None
See application file for complete search history.

(56) References Cited

U.S. PATENT DOCUMENTS

| | | | | |
|---|---|---|---|---|
| 6,965,831 B2 * | 11/2005 | Domany et al. | ............... | 702/19 |
| 7,373,612 B2 * | 5/2008 | Risch et al. | ............... | 715/850 |
| 7,966,327 B2 | 6/2011 | Li et al. | | |
| 2006/0026203 A1 | 2/2006 | Tan et al. | | |
| 2011/0082717 A1 | 4/2011 | Saad et al. | | |
| 2011/0191277 A1 * | 8/2011 | Ag ndez Dominguez et al. | ............... | 706/12 |

OTHER PUBLICATIONS

Agrawal et al. "Automatic Subspace Clustering of High Dimensional Data", 2005, Springer Science + Business Media, pp. 6-33.*
Carpenter et al. "Fuzzy ART: Fast Stable Learning and Categorization of Analog Patterns by an Adaptive Resonance System", 1991, Neural Networks, vol. 4, pp. 759-791.*
Jiang et al. "Mining Coherent Gene Clusters from Gene-Sample-Time Microarray Data", 2004, ACM, pp. 1-10.*
Kim, S. "A GPU based Parallel Hierarchical Fuzzy ART Clustering." Proceedings of the International Joint Conference on Neural Networks. Jul. 31-Aug. 5, 2011. San Jose, California, USA, pp. 2788-2782.
Xu, R.; et al. "Clustering of Cancer Tissues Using Diffusion Maps and Fuzzy ART with Gene Expression Data." Proceedings of the International Joint Conference on Neural Networks. Jun. 1-6, 2008, Hong Kong, China, pp. 183-188.

* cited by examiner

*Primary Examiner* — Hung Q Pham
(74) *Attorney, Agent, or Firm* — Billion & Armitage; Michael A. Collins; Benjamin C. Armitage

(57) ABSTRACT

Methods and systems for improved unsupervised learning are described. The unsupervised learning can consist of biclustering a data set, e.g., by biclustering subsets of the entire data set. In an example, the biclustering does not include feeding know and proven results into the biclustering methodology or system. A hierarchical approach can be used that feeds proven clusters back into the biclustering methodology or system as the input. Data that does not cluster may be discarded. Thus, a very large unknown data set can be acted on to learn about the data. The system is also amenable to parallelization.

15 Claims, 16 Drawing Sheets

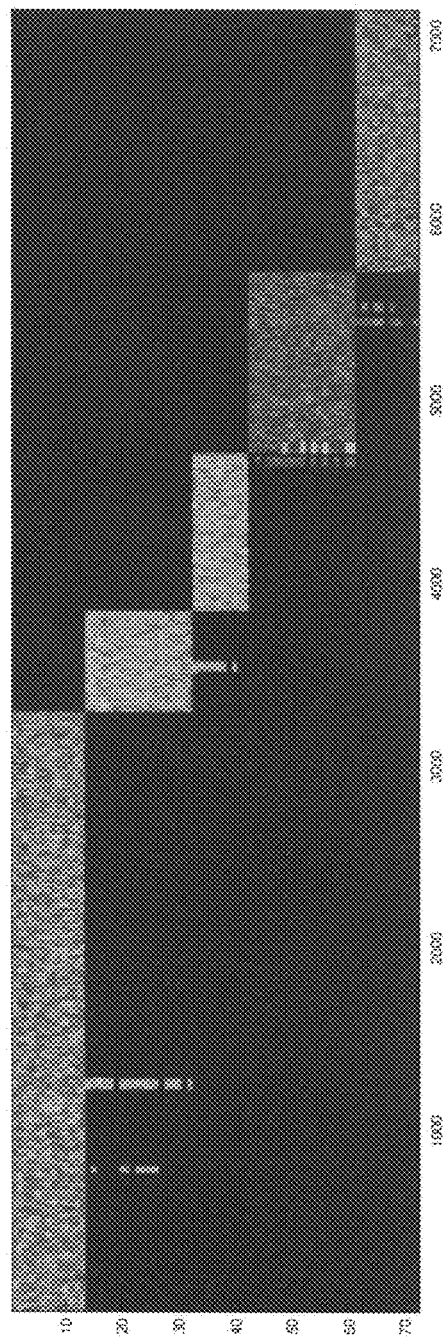

| DATA SET | HF-ART DEPTH | | | | | | |
|---|---|---|---|---|---|---|---|
| | 5 | 10 | 15 | 20 | 50 | 100 | 200 |
| ARBITRARY1(GPU) | 312 | 495 | 498 | 521 | 541 | 581 | 647 |
| ARBITRARY1(GPU) | 40 | 119 | 174 | 234 | 392 | 778 | 1572 |
| ARBITRARY2(GPU) | 4245 | 4788 | 6164 | 6503 | 7206 | 8286 | 10500 |
| ARBITRARY2(GPU) | 1895 | 5879 | 8792 | 11672 | 20227 | 39093 | 76597 |
| 2d-10c(GPU) | 968 | 628 | 752 | 783 | 853 | 962 | 1198 |
| 2d-10c(CPU) | 349 | 694 | 1044 | 1392 | 3548 | 6954 | 14025 |
| 2d-40c(GPU) | 478 | 508 | 597 | 617 | 669 | 751 | 927 |
| 2d-40c(CPU) | 246 | 493 | 738 | 987 | 2463 | 4964 | 9907 |
| 10d-4c(GPU) | 1342 | 1441 | 1750 | 1807 | 1924 | 2097 | 2462 |
| 10d-4c(CPU) | 458 | 921 | 1379 | 1850 | 4647 | 9340 | 18719 |
| 10d-10c(GPU) | 2807 | 3059 | 3866 | 4010 | 4259 | 4688 | 5460 |
| 10d-10c(CPU) | 1186 | 2354 | 3539 | 4735 | 11925 | 23926 | 43974 |
| 10d-40c(GPU) | 1980 | 2213 | 2784 | 2891 | 3038 | 3323 | 3834 |
| 10d-40c(CPU) | 836 | 1681 | 2526 | 3343 | 8406 | 16863 | 31027 |
| ABALONE(GPU) | 2972 | 2867 | 3582 | 3710 | 3929 | 4185 | 4715 |
| ABALONE(CPU) | 519 | 1586 | 2370 | 3153 | 5018 | 10165 | 20214 |

TABLE II

ELAPSED TIME(ms) COMPARISON

*FIG. 13*

METHODS AND SYSTEMS FOR BICLUSTERING ALGORITHM

The present application claims benefit of U.S. Provisional Application No. 61/462,121, filed 28 Jan. 2011, and titled Fast Biclustering Algorithm, which is hereby incorporated by reference for any purpose.

GRANT STATEMENT

This invention was made with government support under Award Numbers: 0725382 and 0836017 awarded by National Science Foundation. The government has certain rights in the invention.

FIELD

This application relates generally to a data integration and analysis method, more specifically, to a high throughput data integration and analysis method based on biclustering or clustering algorithms for research that has significant quantity of data such as biological or biomedical research.

BACKGROUND

Clustering is a data analysis technique that can assist in extracting knowledge from data sets. Clustering can be thought of generally as a process of organizing objects into groups whose members are similar in some way. A cluster is a collection of objects which are "similar" between them and are "dissimilar" to the objects belonging to other clusters. There are numerous areas where the quantity of data does not lend itself to human analysis. Accordingly, computing systems and clustering algorithms are used to learn about the data and assist in extracting knowledge from the data. These algorithms are unsupervised learning algorithms that are executed to extract knowledge from the data. Examples of clustering can include the K-means algorithm (See, J. B. MacQueen (1967): "Some Methods for classification and Analysis of Multivariate Observations, Proceedings of 5-th Berkeley Symposium on Mathematical Statistics and Probability", Berkeley, University of California Press, 1:281-297); Fuzzy c-means (FCM) algorithm (See, J. C. Dunn (1973): "A Fuzzy Relative of the ISODATA Process and Its Use in Detecting Compact Well-Separated Clusters", Journal of Cybernetics 3: 32-57); and model-based algorithms. Clustering is useful to interpret data, because data is being created at a pace at which computers without clustering cannot keep up. Moreover, a significant portion of data is not labeled.

Clustering has been used in the analysis of large data sets, e.g., high-throughput messenger RNA (mRNA) expression profiling with a microarray, which is enormously promising in the areas of cancer diagnosis and treatment, gene function identification, therapy development and drug testing, and genetic regulatory network inference. However, such a practice is inherently limited due to the existence of many uncorrelated genes with respect to sample or condition clustering, or many unrelated samples or conditions with respect to gene clustering.

SUMMARY

Embodiments of the present invention provide a neural-based classifier that can be modified to perform biclustering in an efficient way. Experimental results on multiple human cancer data sets show that the inventive method with the improved algorithm can achieve clustering structures with higher qualities than or compared to those with other commonly used biclustering or clustering algorithms with significantly improved speed.

An example method according to the present disclosure is an unsupervised method for extracting information from a data set, including: creating first clusters of related data from a first subspace of data in the data set; creating second clusters of related data from a second subspace of data in the data set; and building local relationships between the first clusters and the second clusters. The method of above may further include inputting the first cluster into the creating first cluster and creating the second cluster, iteratively. The methods above may further include inputting the second cluster into the creating first cluster and creating the second cluster, iteratively. The first subspace data and the second subspace data are not known correct cluster data. In an example, the first subspace of data may be gene data. In an example, the second subspace of data is sample data. The methods above may include the creating the first clusters is unsupervised and the creating the second clusters is unsupervised. In an example of a method the building the local relationships is unsupervised. In an example, the method may include unsupervised building of the local relationships.

Embodiments of the present disclosure may include systems that can implement the above methods.

In an example, a data interpretation system includes a first module to receive a first subspace of inputs from a data set and to produce first clusters; a second module to receive a second subspace of inputs from the data set and to produce second clusters; and a third module to receive the first clusters and the second clusters, to relate the first and second cluster and to provide feedback to the first module to provide learning control to the system. In an example, the second module received new data without any feedback from the third module. In an example, the first module may be an adaptive resonance theory device and wherein the second module is an adaptive resonance theory device. In an example, any module of the first module, the second module or the third module includes a graphical processing unit. In an example, the data set is a first subset of data that was previously run through the first module and the second module. In an example, the data set is a second subset of the first subset of data that was previously run through the first module and the second module. In an example, the system of the above examples may include a display to display greater correlation of data as part of the data set. In an example, the third module is to build local relationships between the first cluster and the second cluster. In an example, the second dimension inputs are not known correct cluster data.

BRIEF DESCRIPTION OF DRAWINGS

Embodiments are illustrated by way of example and not limitation in the figures of the accompanying drawings, in which like references indicate similar elements and in which:

FIG. 3B shows a Hierarchical Biclustering Adaptive Resonance Theory MAP in accordance with an example embodiment;

FIG. 13 is a table showing the point where the GPU performance exceeds the CPU performance as a function of data set and depth;

DETAILED DESCRIPTION

Example apparatuses, devices, methods and systems are described. In the following description, for purposes of explanation, numerous specific details are set forth in order to provide a thorough understanding of example embodiments. It will be evident, however, to one skilled in the art that the present invention can be practiced without these specific details.

As an overview, biclustering, accordingly to embodiments of the present disclosure, offers a solution to some standard clustering problems by performing simultaneous clustering on both dimensions so that the relations of clusters of genes and clusters of samples or conditions are established. Biclustering may then automatically integrate feature selection to clustering without any prior information from the data. However, the NP-complete computational complexity raises a great challenge to computational methods to find such local relations. Here, we propose and demonstrate that a neural-based classified, Fuzzy ARTMAP, can be modified to perform biclustering in an efficient way, leading to a biclustering algorithm (BARTMAP). Experimental results on the multiple human cancer data sets show that BARTMAP can achieve clustering structures with higher qualities than other commonly used biclustering or clustering algorithms, while effectively disclosing the relations between genes and conditions or samples.

Figure 1:
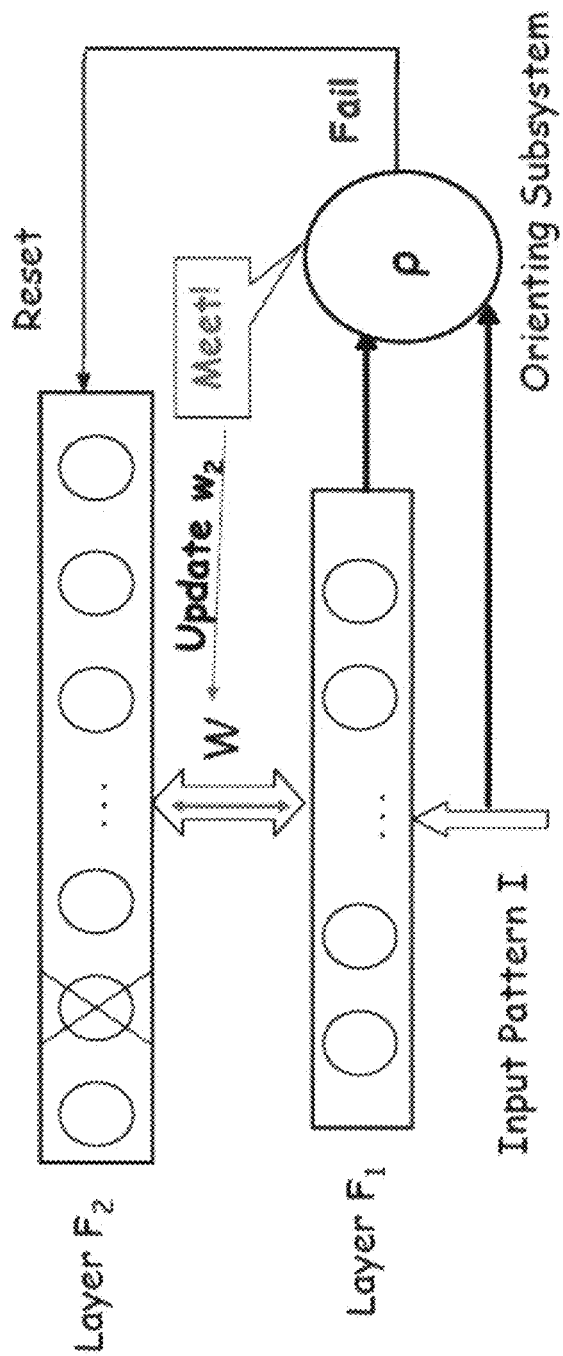
FIG. 1 is a schematic view of an Adaptive Resonance Theory (ART) system in accordance with an example embodiment.

FIG. 1 shows a schematic structure of a system for Fuzzy Adaptive Resonance Theory (ART). Fuzzy ART performs fast, online, unsupervised learning by clustering input patterns, admitted in Layer $F_1$, into hyper-rectangular clusters, stored in Layer $F_2$. Both layers are connected via adaptive weights W. The orienting subsystem is controlled by the vigilance parameter p. The Fuzzy ART system includes two-layer neurons, the feature representation field $F_1$ and the category representation field $F_2$. The neurons in layer $F_1$ are activated by the input pattern and normalized with the complement coding rule (Carpenter, G., Grossberg, S., & Rosen, D. (1991). Fuzzy ART: Fast stable learning and categorization of analog patterns by an adaptive resonance system. Neural Networks, 4, 7 9-771, hereby incorporated by reference). The prototypes of the formed clusters are stored in layer $F_2$. The neurons in layer $F_2$ that are already being used as representations of input patterns are said to be committed. Correspondingly, the uncommitted neuron encodes no input patterns. The two layers are connected via adaptive weights Wj, emanating from node j in layer $F_2$, which are initially set as 1. After an input pattern is presented, the neurons (including a certain number of committed neurons and one uncommitted neuron) in layer $F_2$ compete by calculating the category choice function $$T_j = \frac{|x \wedge w_j|}{\alpha + |w_j|},$$

where $\wedge$ is the fuzzy AND operator defined by $$(x \wedge y)_i = \min(x_i, y_i),$$

and $\alpha > 0$ is the choice parameter to break the tie when more than one prototype vector is a fuzzy subset of the input pattern, based on the winner-take-all rule, $$T_J = \max_j \{T_j\}.$$

The winning neuron, J, then becomes activated, and an expectation is reflected in layer $F_1$ and compared with the input pattern. The orienting subsystem with the pre-specified vigilance parameter $\rho$ ($0 \leq \rho \leq 1$) determines whether the expectation and the input pattern are closely matched. If the match meets the vigilance criterion, $$\rho \leq \frac{|x \wedge w_J|}{|x|}$$

weight adaptation occurs, where learning starts and the weights are updated using the following learning rule, $$w_J(new) = \beta(x \wedge w_J(old)) + (1-\beta)w_J(old),$$

where $\beta \in [0, 1]$ is the learning rate parameter and $\beta=1$ corresponds to fast learning. This procedure is called resonance, which suggests the name of ART. On the other hand if the vigilance criterion is not met, a reset signal is sent back to layer $F_2$ to shut off the current winning neuron, which will remain disabled for the entire duration of the presentation of this input pattern, and a new competition is performed among the remaining neurons. This new expectation is then projected into layer $F_1$, and this process repeats until the vigilance criterion is met. In the case that an uncommitted neuron is selected for coding, a new uncommitted neuron is created to represent a potential new cluster.

An example of clustering is described in "Clustering of Cancer Tissues Using Diffusion Maps And Fuzzy ART with Gene Expression Data" by Rui Xu, Steven Damelin, and Donald C. Wunsch II, published in Neural Networks, 2008. UCNN 2008. (IEEE World Congress on Computational Intelligence), hereby incorporated by reference for any purpose.

Figure 2:
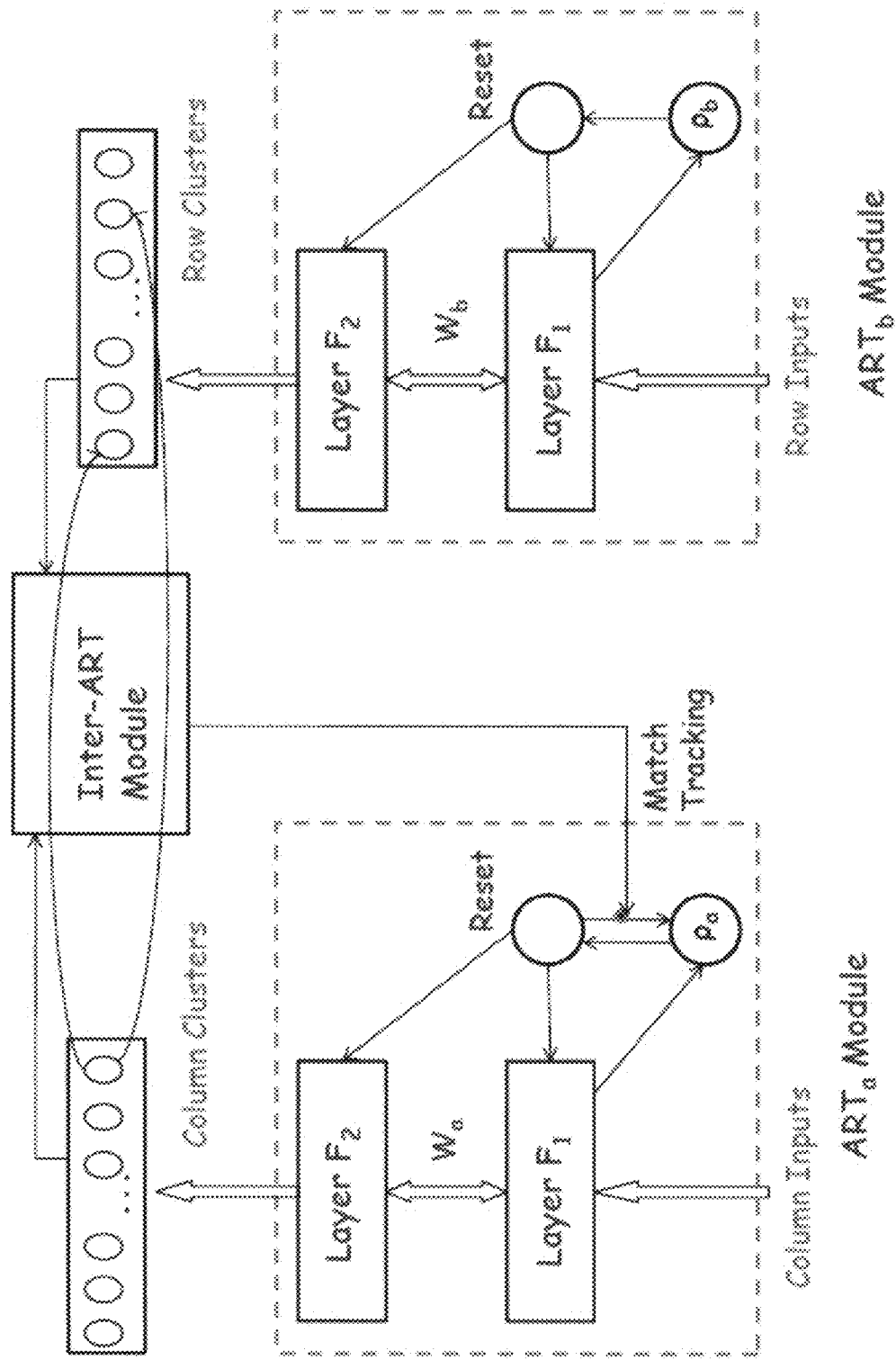
FIG. 2 is a schematic view of a Biclustering Adaptive Resonance Theory MAP (BARTMAP) system in accordance with an example embodiment.

FIG. 2 shows a schematic structure of a system for Biclustering Adaptive Resonance Theory MAP (BARTMAP). In an example, the first clusters, e.g., gene clusters, are first formed in the $ART_b$ module and the second clusters, e.g., sample clusters, are formed in the $ART_a$ module with the requirement that the members in the same cluster should behave similarly across at least of one of the formed first clusters. The match tracking mechanism is the inter-art module. The match tracking mechanism will increase the vigilance parameter of the $ART_a$ module in the case of a failure to such a condition. In the present biclustering data is input into both the $ART_a$ module and $ART_b$ module. In some conventional methods, known data, e.g., known clusters, is input into $ART_b$ module. The inter-art module finds relationships between the clusters using unsupervised learning, which may be part of embodiments of the present invention.

BARTMAP may include the basic theory and the functions of Fuzzy ARTMAP, but with a different focus on clustering in at least two subspaces (e.g., the both dimensions of FIG. 16) rather than on supervised classification for which Fuzzy ARTMAP is generally used. A Fuzzy ARTMAP network consists of two Fuzzy ART modules ($ART_a$ and $ART_b$) interconnected via an inter-ART module, or the map field module. See FIG. 2. In the context of supervised classification, the input pattern (e.g., unclassified or unclustered data) is presented to the $ART_a$ module and the corresponding label (e.g., a known pattern) is presented to the $ART_b$ module. For gene expression data, the input patterns can be either genes or samples, but not both, depending on the interests of the users. The vigilance parameter of $ART_b$ is set to 1, which leads to the representation of each label as a specific cluster. The information regarding the input-output associations is stored in the weights $w^{ab}$ of the inter-ART module. The $j^{th}$ row of the weights of the inter-ART module $w_j^{ab}$ denotes the weight vector from the jth neuron in $ART_a$ to the map field. When the map field is activated, the output vector of the map field is $$x^{ab} = y^b \wedge w_j^{ab},$$

where $y^b$ is the binary output vector of field $F_2$ in $ART_b$ and $y_i^b = 1$ only if the $i^{th}$ category wins in $ART_b$. Similar to the vigilance mechanism in $ART_a$, the map field also performs a vigilance test, such that if $$\rho_{ab} > \frac{|x^{ab}|}{|y^b|},$$

where $\rho_{ab}(0 \leq \rho_{ab} \leq 1)$ is the map field vigilance parameter, a match tracking procedure is activated, where the $ART_a$ vigilance parameter $\rho_a$ is increased from its baseline vigilance $\rho_{a[bar]}$ by a number $\sigma(0 < \sigma << 1)$. This procedure assures the shut-off of the current winning neuron in $ART_a$, whose prediction does not comply with the label represented in $ART_b$. Another $ART_a$ neuron will then be selected, and the match tracking mechanism will again verify whether it is appropriate. If no such neuron exists, a new $ART_a$ category is created. Once the map field vigilance test criterion is satisfied, the weight $w_j^{ab}$ for the neuron J in $ART_a$ is updated by the following learning rule:

$$w_j^{ab}(\text{new}) = \gamma(y^k \wedge w_j^{ab}(\text{old})) + (1-\gamma)w_j^{ab}(\text{old}),$$

where $y \in [0, 1]$ is the learning rate parameter. Note that with fast learning ($y=1$), once neuron J learns to predict the $ART_b$ category I, the association is permanent, i.e., $w_j^{ab}=1$ for all input pattern presentations.

In a test phase where only an input pattern is provided to $ART_a$ without the corresponding label to $ART_b$, no match tracking occurs. The class prediction is obtained from the weights of the winning $ART_a$ neuron. However, if the neuron is uncommitted, the input pattern cannot be classified solely based on prior experience.

Similar to Fuzzy ARTMAP, BARTMAP also includes of two Fuzzy ART modules communicated through the inter-ART module (see FIG. 2), but the inputs to the $ART_b$ module are second data subspace, e.g., genes (rows), instead of the labels as in traditional Fuzzy ARTMAP. As such, the inputs to the $ART_b$ module are samples, although we can exchange the inputs to the $ART_a$ and $ART_b$ module and perform the similar procedures as described as follows to identify relations between first (e.g., gene) clusters and second (e.g., sample) clusters. An idea of BARTMAP is to integrate the clustering results on the dimensions of columns and rows of the data matrix from certain clustering algorithms in order to create biclusters. This is more conceptually simpler than other types of biclustering algorithms. In other words, BARTMAP can be considered as a combination of clustering with automatic feature selection without any prior information if we treat one dimension (e.g., a column) as data objects and the other dimension (row) as description features. Note that the feature selection in biclustering is different from the feature selection that is usually considered in supervised classification in that biclustering selects different subsets of features for different clusters of data objects while the standard feature selection chooses a subset of features from the candidate pool for all data objects. BARTMAP, accordingly to embodiments of the present disclosure, with the objective focusing on the clustering of a set of samples and the identification of related gene clusters for each sample cluster simultaneously.

Figure 5:
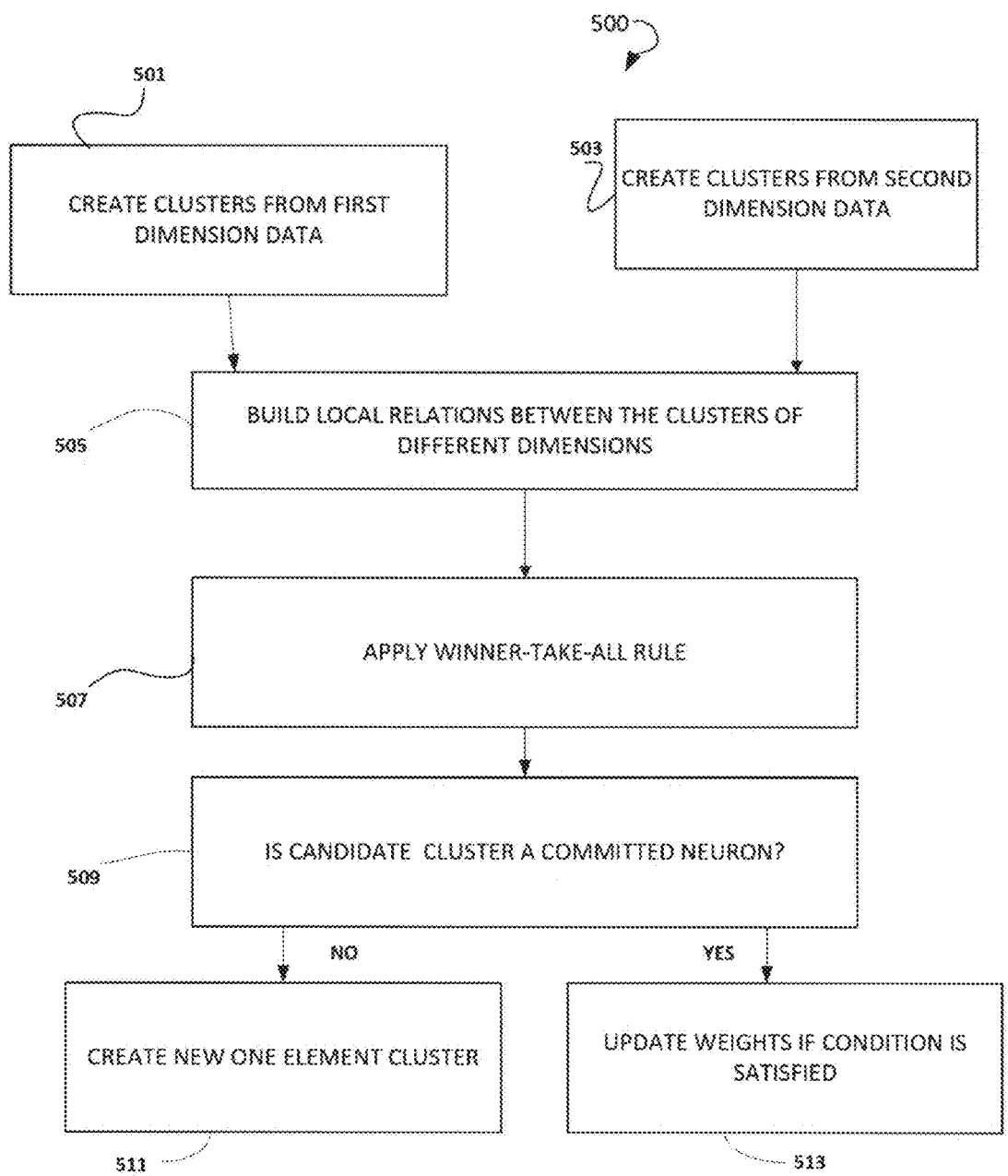
FIG. 5 is a flow chart of a process in accordance with an example embodiment.

FIG. 5 shows a flow of a method 500 for processing large data sets that have a plurality of dimensions, according to an embodiment of the present disclosure. At 501, first clusters are created in a first dimension of the data set. At 503, second clusters are created in a second dimension of the data set. At 505, local relationships between the first and second clusters are built. At 507, a selection is performed. In an example, the winner-take-all rule is applied with the requirement that the vigilance test be passed. At 509, a decision on the placement of the candidate cluster is made. If the candidate cluster corresponds to a non-committed neuron, then a new sample cluster is created, 511. If the candidate cluster is not committed a committed neuron, then the weights may be updated if a condition is met, 513.

An example of the method 500 will now be explained using gene data. The first step of a BARTMAP process, e.g., using the structure of FIG. 2, is to create a set of Kg gene clusters $G_{ib}$, $i=1, \ldots K_g$, for genes by using the $ART_b$ module. In other words, only $ART_b$ module functions as a standard Fuzzy ART in this step. The objective of the following step is to create $K_s$ sample clusters $S_j$, $j=1, \ldots, K_s$ for M samples within the $ART_a$ module, while building the local relations between the sample and gene clusters. Upon the presentation of a new sample, the candidate sample cluster that is eligible to represent this sample is determined based on the winner-take-all rule, with the requirement to passing the vigilance test. If this candidate cluster corresponds to an uncommitted neuron, learning will occur to create a new one-element sample cluster that represents this sample. On the other hand, if it is a committed neuron that is picked as the candidate, the method, autonomously using a computing device, only updates the weights of this neuron if the following condition is satisfied: A sample is absorbed into an existing sample cluster if and only if it displays similar behavior or patterns to the other members in the cluster across at least one gene cluster formed in $ART_b$ module.

The similarity between the new sample sk and the sample cluster $S_j=\{s_{j1}, \ldots, s_{jM1}\}$ with $M_j$ samples across a gene cluster $G_i=\{g_{i1}, \ldots, g_{1Ni}\}$ with $N_i$ genes being calculated as the average Pearson correlation coefficient between the sample and all the samples in the cluster $$\rho_{kj} = \frac{1}{M_j} \sum_{l=1}^{M_j} \rho_{k,jl}$$

where $$\rho_{k,jl} = \frac{\sum_{i=1}^{N_i} (e_{s_k g_g} - \overline{e_{s_k G_l}})(e_{s_\phi g_g} - \overline{e_{s_\phi G_l}})}{\sqrt{\sum_{i=1}^{N_i} (e_{s_k g_g} - \overline{e_{s_k G_l}})^2} \sqrt{\sum_{i=1}^{N_i} (e_{i_\phi g_k} - \overline{e_{l_\phi G_l}})^2}}$$

and $$\overline{e_{s_k G_l}} = \frac{1}{N_i} \sum_{i=1}^{N_i} e_{s_g g_g}$$

$$\overline{e_{s_\phi G_l}} = \frac{1}{N_i} \sum_{i=1}^{N_i} e_{s_\phi g_\phi}$$

The sample $s_k$ is enclosed in the cluster Sj only when $\rho_{kj}$ is above some threshold η and learning will occur following the updating rule of Fuzzy ART.

If the sample does not show any similar behavior with the sample cluster the winning neuron represents for any clusters of genes, the match tracking mechanism will increase the $ART_a$ vigilance parameter $\rho_a$ from its baseline vigilance by a small number, e.g., as done in Fuzzy ARTMAP. The current winning neuron in $ART_a$ will be shut off as a consequence of the continuous increase of the vigilance parameter, which will force the sample to be included into some other cluster, or to create a new cluster for the sample if no existing sample cluster an ever match well with it.

Biclustering performs simultaneous clustering on features and data automatically integrating feature selection to clustering without any prior information, so that the relations of clusters of unsupervised labels (for example, genes) and clusters of data (for example, samples or conditions) are established. However, typical approaches have NP-complete computational complexity, which raises a great challenge to computational methods for identifying such local relations. The present inventors have recognized and discovered that a neural-based classifier can be modified to perform biclustering in an efficient way. Experimental results on multiple human cancer data sets show that the algorithm can achieve clustering structures with higher qualities than or compared to those with other commonly used biclustering or clustering algorithms. The high speed of this algorithm is a considerable advantage.

While some of the above examples describe genetic and medical data analysis using the methods, algorithms and systems described herein, the present disclosure can also be used for social network analysis, computer security applications, other security applications, and data mining.

It is further believed that biclustering as described herein can result in faster processing than conventional data processing and can use less memory resources. The biclustering can also be used in embedded or real-time systems. The biclustering as described herein can also be used in parallel, which will also increase the speed. All of these features should result in greater accuracy as well as an increase in speed.

Figure 3A:
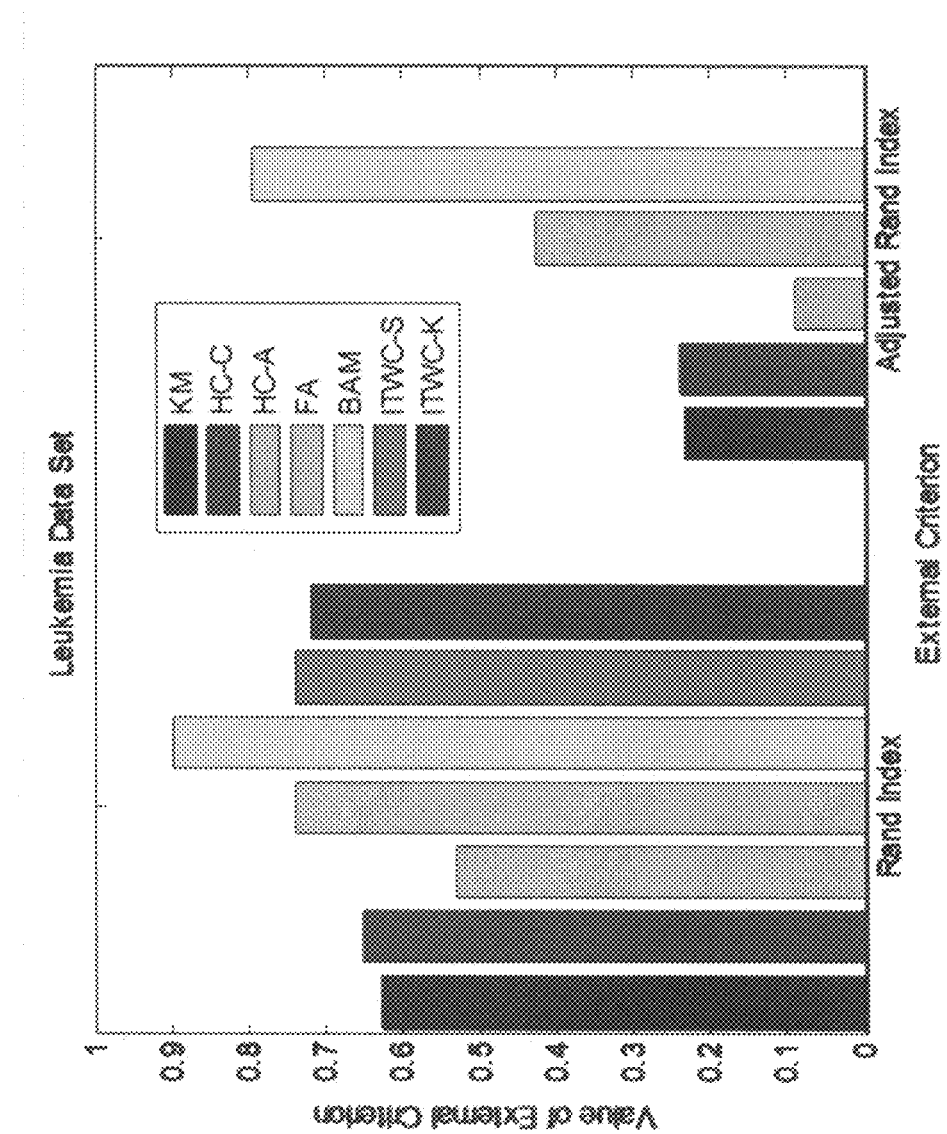
FIG. 3A shows a table of a data set related to Leukemia in accordance with an example embodiment.

FIG. 3A shows a BARTMAP (BAM) produced using the structures and methods as described herein on the leukemia data set in terms of Rand and adjusted Rand index. The results are compared with those from Fuzzy ART (FA), interrelated two-way clustering with SOFM (ITWC-S) and K-means (ITWC-K), K-means (KM), hiearchical clustering with complete linkage (HC-C), and hierarchical clustering with average linkage (HC-A).

The proposed methods and structures described herein were applied to three benchmark data sets in gene expression profile-based cancer research. The first data set is the leukemia data set that consists of 72 samples, including bone marrow samples, peripheral blood samples and childhood acute myeloid leukemia (AML) cases. Twenty-five of these samples are acute myeloid leukemia (AML). Forty-seven samples are acute lymphoblastic leukemia (ALL), composed of two subcategories due to the influences of T-cells and B-cells. The expression levels for 7129 genes (including 312 control genes) were measured across all the samples by high-density oligonucleotide microarrays. The data are expressed as the gene expression matrix $E=\{e_{ij}\}_{7129 \times 72}$, where $e_{ij}$ represents the expression level of gene i in tissue sample j. Linear transformation is used to scale all inputs into the interval [0,1], as BARTMAP requires.

Because the real partitions of the datasets used here are already known, the performance of the BARTMAP can then be evaluated by comparing the resulting clusters with the real structures in terms of external criteria. In this test of the methods described herein, both the Rand index and the adjusted Rand index, which is designed to correct the Rand index for randomness, are used.

Assuming that P is a pre-specified partition of dataset X with N data objects, which is also independent from a clustering structure C resulting from the use of the BARTMAP algorithm/methodology for a pair of data objects $x_i$ and $x_j$, results in four different cases based on how $x_i$ and $x_j$ are placed in C and P.

Case 1: $x_i$ and $x_j$ belong to the same clusters of C and the same category of P.

Case 2: $x_i$ and $x_j$ belong to the same clusters of C but different categories of P.

Case 3: $x_i$ and $x_j$ belong to different clusters of C but same category of P.

Case 4: $x_i$ and $x_j$ belong to different clusters of C and a different category of P.

Correspondingly, the number of pairs of samples for the four cases are denoted as a, b, c, and d, respectively. Because the total number of pairs of samples is M(M−1)/2, denoted a L, we have a+b+c+d=L. The Rand index and the adjusted Rand index can then be defined as follows, with larger values indicating more similarity between C and P, $$R = (a+d)/L,$$

$$\text{Adj\_R} = \frac{\binom{M}{2}(a+d) - ((a+b)(a+c) + (c+d)(b+d))}{\binom{M}{2}^2 - ((a+b)(a+c) + (c+d)(b+d))}.$$

FIG. 3A summarizes the best performance of BARTMAP on the leukemia data set, compared with the results from another state-of-the-art biclustering algorithm, interrelated two-way clustering (ITWC) (Tang & Zhang, 2005, "Interrelated two-way clustering and its application n gene expression data", *International Journal on Artificial Intelligence Tools*, 14, 577-597.), which is based on either self-organizing feature maps (SOFMs) (Kohonen, 2001, "Self-organizing maps" (3rd ed.). Berlin: Springer) or the K-means algorithm. The performance with commonly used clustering algorithms, such as K-means (KM) and hierarchical clustering algorithms with complete linkage (HC-C) or average linkage (HC-A), is also included. The results of shown in FIG. 3 are also compared to BARTMAP (BAM) with its basic module, Fuzzy ART (FA), to investigate how the performance is improved with the integration of feature selection. The performance is evaluated based on both the Rand index and the adjusted Rand index, except for the ITWC approach (ITW-S and ITWC-K), for which the result based on the adjusted Rand index are not reported. However, since the Rand index is usually over optimistic compared with the adjusted Rand index, it is estimated that the adjusted Rand index values for ITWC approach should be at least less than the values of the Rand index. It is clearly shown in the figure that BARTMAP has achieved the best performance in the leukemia data analysis in terms of both the Rand index and the adjusted Rand index. Particularly for the adjusted Rand index, the next value (FA) close to that of BARTMAP is 0.4254, which is far less than the value of BARTMAP (0.78926). Comparing BART MAP with ITWC, BARTMAP has an increase of 15.88%.

FIG. 3B shows a heat map resulting from Hierarchical Biclustering Adaptive Resonance Theory MAP in accordance with an example embodiment. The data represented relates gene sample data to the leukemia sample data processed according to the methods described herein. The brighter the image area, the more correlated the gene is to leukemia.

Figure 4:
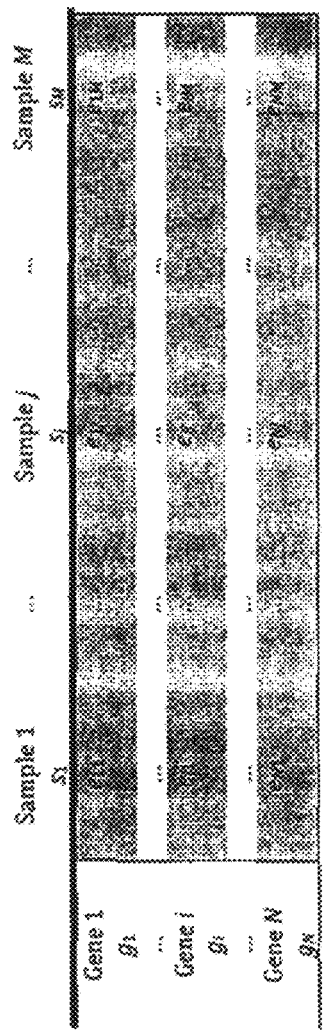
FIG. 4 is table related to a gene expression data matrix in accordance with an example embodiment.

FIG. 4 is table related to a gene expression data matrix in accordance with an example embodiment. Each gene $g_i$ corresponds to a vector $g_i = (e_{i1}, \ldots, e_{iM})$ and each sample corresponds to a vector $s_i = (e_{1j}, \ldots, e_{Nj})$, where each element $e_{ij}$ in the matrix corresponds to the expression value of gene $g_i$ in sample $s_j$. More specifically, the expression levels of a large set of genes are measured across a set of conditions or samples and the obtained gene expression data are organized as a data matrix with rows corresponding to genes and columns corresponding to samples or conditions. Given a gene expression data matrix E=(G, S), with G={$g_1, \ldots, g_x$} representing a set of N genes or rows and S={$s_1, \ldots, s_M$} representing a set of M samples (which can also be conditions) or columns (see FIG. 4), a gene or row cluster is then a subset of rows defined on all columns, denoted as Cxs=(X, S), where X ⊆ G is a subset of genes. Similarly, a sample or column cluster is a subset of columns defined across all rows, denoted as $C_{GY}$=(G, V), where Y ⊆ S is a subset of samples.

Such a data matrix and the corresponding row and column cluster definition can be generalized as a data matrix for many other applications. However such a practice is inherently limited because according to our general understanding of cellular processes, only a subset of genes is involved with a specific cellular process, which becomes active only under some experimental conditions, while microarrays are generally not specifically designed to meet the requirements of an experiment of interest. Considering for example in gene expression profile-based cancer diagnosis, only a subset of genes is related to some cancer type while numerous genes are considered as irrelevant. In this case, the inclusion of all genes in sample clustering or all samples in gene clustering not only increases the computational burden, but could impair the clustering performance due to the effect of these unrelated genes or samples, which are treated as noise.

BARTMAP (Biclustering ARTMAP) to perform biclustering on large data sets, e.g., gene expression data. A BARTMAP is an improvement on a neural-based classifier, Fuzzy ARTMAP, for supervised classification. Similar to Fuzzy ARTMAP, BARTMAP is based on Adaptive Resonance Theory (ART) (Carpenter & Grossberg, 1987; Grossberg, 1976), which is a learning theory hypothesizing that resonance in neural circuits can trigger fast learning and which was developed as a solution to the plasticity-stability dilemma. BARTMAP displays many attractive characteristics. First, BARTMAP scales very well with large-scale data analysis while maintaining efficiency. As the computational complexity for its ART modules is O(N log N) or O(N) for one pass variant (Mulder & Wunsch, 2003), the overall computational cost for BARTMAP is relatively low. Each ART module (e.g., FIG. 1 or FIG. 2) can dynamically and adaptively generate clusters without the requirement of specifying the number of clusters in advance as in the classical K-means algorithm. Furthermore, BARTMAP is an exemplar-based, transparent learning model. During its learning, the architecture summarizes data via the use of exemplars in order to accomplish its learning objective. This ability contrasts with other, opaque neural network architectures for which it is generally difficult to explain why an input produces a particular output. Another feature of BARTMAP is its ability to detect atypical patterns during its learning. The detection of such patterns is accomplished via the employment of a match-based criterion that decides to which degree a particular pattern matches the characteristics of an already-formed category in BARTMAP. Finally, BARTMAP is far simpler to implement than, for example, backpropagation for feed-forward neural networks and the training algorithm of support vector machines.

An example that includes some of the methods and structures will now be described. In particular, a graphical processing unit (GPU) can be used as the device to execute the methods for clustering, biclustering and hierarchical biclustering. Other processing units can also be used. GPU programming, e.g., executing stored instructions in a computing device, is useful for population based algorithms.

Fuzzy Adaptive Resonance Theory (ART) algorithms can be used for hierarchical clustering. Fuzzy ART can implement an increase in speed and introduce scalability and parallel implementation. Embodiments of the present disclosure implement hierarchical fuzzy ART using GPU engines.

Figure 6:
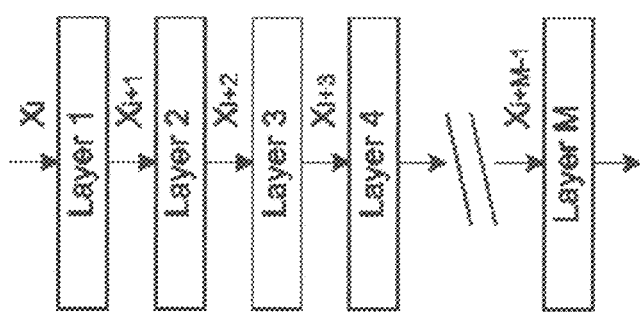
FIG. 6 is schematic view of hierarchical fuzzy ART system in accordance with an example embodiment.

FIG. 6 shows and example of architecture to execute Fuzzy ART. This architecture can be similar to a pipelining structure. Such an ART architecture as shown in FIG. 6, which can be trained sequentially but can also execute in parallel. The first layer, layer 1, which is also the root node, starts with a sample ($X_I$) and once the training is finished for the first layer, the root ART unit of the first layer passes the sample that has won the training ($X_{I+1}$) to the next node in Layer 2, e.g., a child node corresponding to which category of the sample that has won in the training. Each layer loads the proper ART unit for the training for different samples as the winning category varies.

Adaptive Resonance Theory (ART) is an unsupervised learning method which vanquishes the "stability-plasticity dilemma". ART is capable of learning arbitrary data in a both stable and self-organizing manner. ART1 deals with binary data, whereas Fuzzy ART deals with arbitrary data. Embodiments of the present disclosure implements Fuzzy ART. Before the training and ART unit, the data passes through a pre-training process step, scaling the data to fit in the range of [0,1]. The weight vectors $w_j$ are initialized to be all 1. The value x is an input sample. In category choice, the competition in F2 is calculated using the following formula $$T_i = \frac{|x \wedge w_j|}{\alpha + |w_j|},$$

where ˆ is the fuzzy AND operator defined by $$(x \hat{\ } y)_i = \min(x_i, y_i),$$

and $\alpha > 0$ is the choice parameter. By the winner-take-all competition, $$T_j = \max\{T_j | \forall_j\}$$

Figure 7:
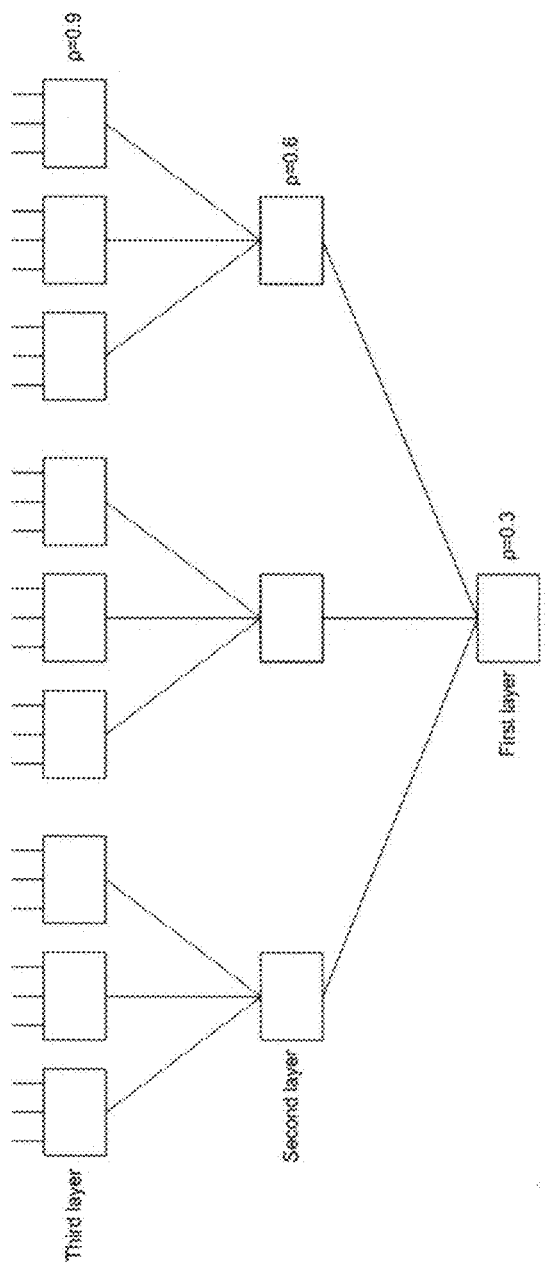
FIG. 7 is a diagram of a hierarchy of ART units, wherein the input pattern is registered at the bottom (first layer) and is sequentially fed only to those ART units in the hierarchy of "winning" $F_2$ units from the parent node in accordance with an example embodiment.

The winning neuron J becomes activated and is fed back to layer F1 for the vigilance test. If $$\rho \leq \frac{|x \wedge w_J|}{|x|},$$

resonance occurs. Then in layer $F_2$, the input x is categorized to J and the network is trained by the following learning rule, $$w_J(\text{new}) = \beta(x \hat{\ } w_J(\text{old})) + (1-\beta) w_J(\text{old}),$$

where $\beta(0 \leq \beta \leq 1)$ is the learning rate. If neuron J does not meet the match criterion, it will be reset and excluded during the presentation of the input within the vigilance test. The hierarchical fuzzy ART network is shown in FIG. 7 and includes a plurality of Fuzzy Art units. FIG. 7 shows a first example where an input pattern is registered at the bottom in Layer 1 and is sequentially fed from a parent node in Layer 1 only to those FA units in the hierarchy of "winning" FA units in Layer 2. The subsequent layers reiterate this methodology. In another example, the methodology can be operated in reverse for clustering. A large amount of data is input into the top most layer, Layer 3 in FIG. 7. The Layer 3 FA units clusters the data input and then feeds the next layer, here Layer 2 in FIG. 7. The Layer 2 FA units clusters the data input from Layer 3 and then feeds the result to Layer 1. It will be recognized that the present disclosure is not limited to three layers and can be expanded to any plurality of layers. The hierarchy of ART units illustrated in FIG. 7 is done in order to split the clusters more finely by increasing the vigilance. Stated another way the sensitivity is increased the data is passed to a next level relative to a prior level. An example of a modular multi-layer network architecture composed of ART networks (HART, for "Hierarchical ART").

Figures 8, 9:
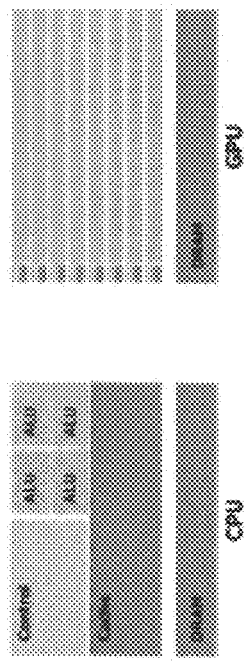
FIG. 8 is diagrams showing structure differences between a central processing unit and a graphics processing unit, which can be used to execute embodiments of the present invention.
FIG. 9 is a table showing data used in an experiment using the BARTMAP methodology described herein.

The desire of displaying a 3D world on computers in real-time greatly increased the computational ability of graphics processors. FIG. 8 illustrates design difference between CPUs and GPUs. A kernel which is the set of operations defined in GPU processors can be programmed and executed simultaneously in different threads. A single NVIDIA Fermi GPU theoretically is capable of containing up to 67,107,840 threads.

There may be constraints in using a GPU, for example, direct memory access between the host processor (CPU) and the graphic processor (GPU) is not possible and thus to handle certain data in other sides, data transfer is required either from CPU to GPU or vice versa. Because such a data transfer rate is relatively slow, data transition should be minimized. The lack of dynamic pointer and array generation inside the kernel may limit the GPU.

In order to increase the speed of processing, parallalization of Hierarchical Fuzzy ART (HF-ART) may be implemented. In the example of FIG. 6, the layers (Layers 1-Layer M), are distributed among the GPU threads. Each layer is not an individual module but behaves as a controller to call up required FA on every diverse states. Layer 1 is exclusively assigned to the root FA node. Every time an input passes through a layer, the working FA module in the layer emanates the adapted category back to the layer. Then that layer assigns the child FA node and broadcasts the node ID and the input ID to the adjacent lower layer while receiving the new assignment from the upper layer. Such a methodology can be a form of pipelining. Algorithm 1, below, is the pseudocode of the kernel in the program.

Algorithm 1 Layer Behavior

```
if Li assignment exists then
    call FA module
    call input
    do FA training
    set Li+1:FAJ ,input
end if
if layer is root then
    idData++
else
    wait assignment
end if
```

After an initialization step, the first data will be registered in root FA (e.g., Layer 1). Once the training is completed, the layer will attempt to find the ID of the corresponding child FA module which is not set yet. In generic CPU programming, generating a child node can be done by allocating a new pointer and cross referring between the parent and child node or by vector template coding. However, these methods are not used in a kernel lever. Accordingly, a semi-dynamic pointer method is applied. Semi-dynamic arrays have a fixed maximum size set and an tracking integer is defined to record the used amount in contrast to true dynamic arrays.

An example execution of the present disclosure was performed. In the present example, the memory size of the graphic card used for an experiment to execute the present method was about 1.6 GB. The contents occupying the memory VRAM within the program are the data sample vectors, layer states and other very small entries such as the kernel itself, registers and local variables in each kernel. A million samples of 4 dimensional float vector take up only 32 MB. As a result, the rest of the memory can be declared for the FA modules. The number of maximum FA modules depends on the dimension of the sample vector as well as the preset number of maximum category allowed. In the example execution of the method, 1.5 million FA modules could be pre-declared.

While application of semi-dynamic array can improve the performance, it can also introduce a parallel feature known as a race condition may hinder the tracking of the maximum size. Assuming a situation when all of the layers need to generate a new child FA module, the threads will attempt to assign a child node in the same place as they are running in parallel. Thus, concurrent or sequential coding of instructions can be needed in order to correctly assign a child node and to keep the tracker in control. To reduce the non-parallelism, the throughput of the child id finder which runs right after the FA trainer is limited as much as possible. Limiting can be performed, for example, by pseudocode in Algorithm 2, Child ID Finder Algorithm 2 Child ID Finder

```
for i = ↗ layer do
    if new child needed then
        idChild ← tracker
        tracker++
    end if
end for
```

Once the child node ID is setup, the layer behavior kernel reruns to finish the task. With the child ID finder, the entire program procedure is depicted in Algorithm 3, Parallel Hierarchical Fuzzy ART.

Algorithm 3 Parallel Hierarchical Fuzzy ART

```
init setting
memcpy(host → device)
for i = 1 to nDATA + nLayer − 1 do
    FA Trainer( )
    childIDFinder( )
    setNextAssignment( )
end for
memcpy(device → host)
```

Using the above structure and methodology, experiments were run. The computing device used in the experiments was an Intel Xeon E5620 Quad Core CPU with 12 GB RAM and NVIDIA Geforce GTX 480, which can represent both CPU and GPU. The data was two sets of arbitrary generated data, "abalone" data from UCI Machine Learning Repository and five sets of the synthetic data developed by Handl and Knowles ("Improving the scalability of multiobjective clustering," Proceedings of the Congress on Evolutionary Computation 2005, vol. 3, pp. 2372-2379, 2005) are used for the performance testing. The depths of the hierarchy were set in the range of 5, 10, 15, 20, 50, 100 and 200. For the simulation, only the vigilances of each layer varied linearly in the range of [0.3, 0.9]. The learning rate and the choice parameter were set as 0.8 and 0.1, respectively. The elapsed times on CPU platform and GPU platform were measured differently. The initial setup time for both platforms were excluded but the consumed time while copying data to and from the GPU was included on the GPU performance aspect. The features of the data used for the simulation are summarized in FIG. 9.

Figure 10:
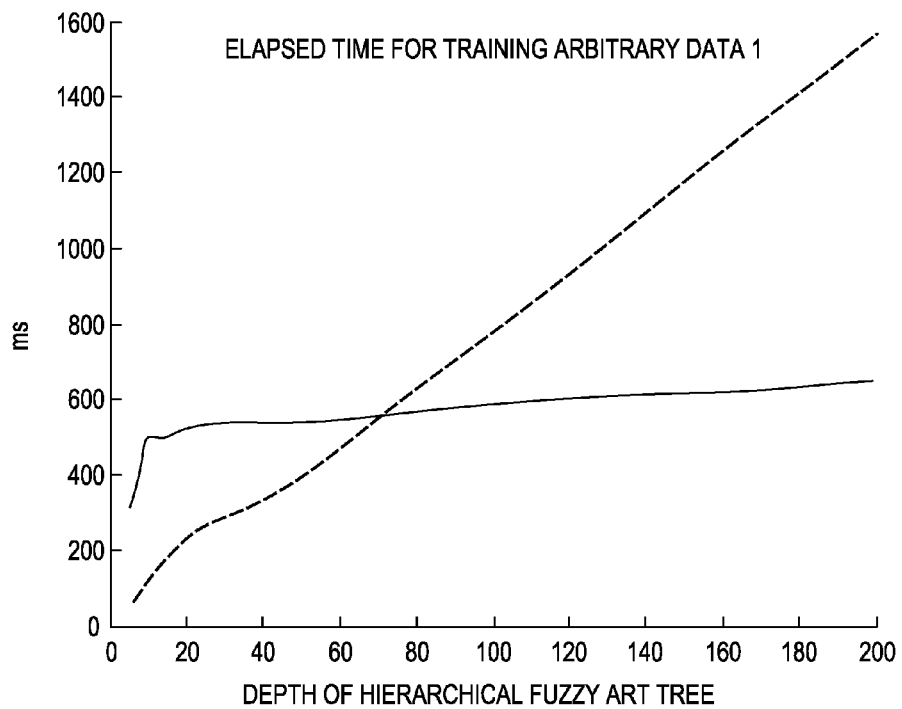
FIG. 10 is a graph showing elapsed time as a function of depth of the hierarchical ART tree for both a central processing unit (CPU) in dotted line and a graphics processing unit (GPU) in dashed line when both CPU and GPU are functioning using example embodiments of the present invention on a first data set.
Figure 11:
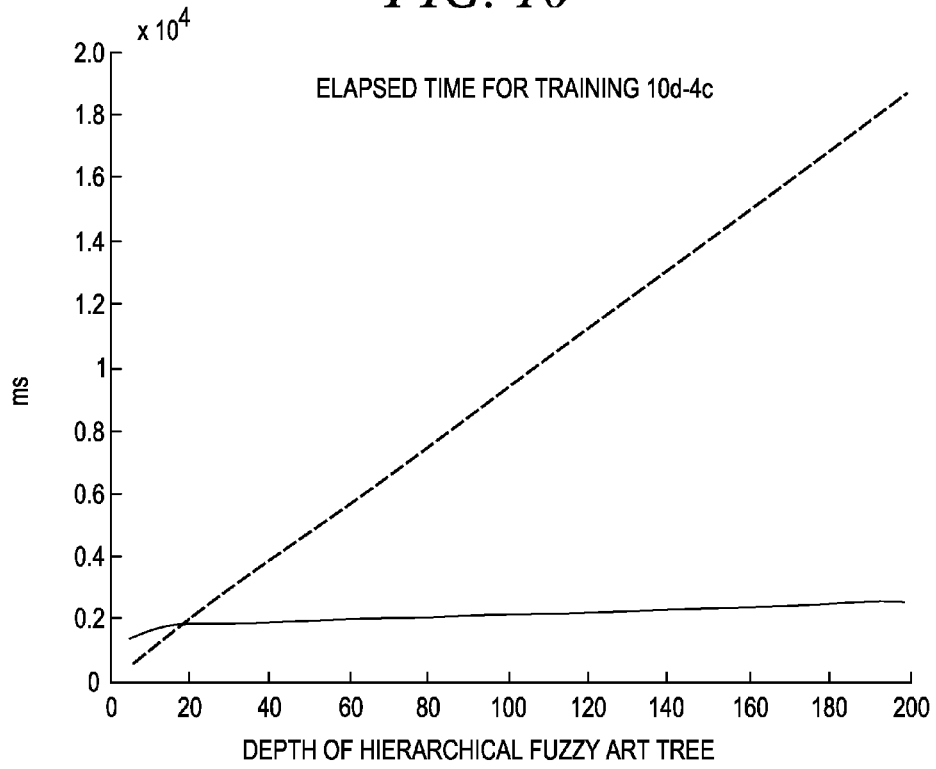
FIG. 11 is a graph showing elapsed time as a function of depth of the hierarchical ART tree for both a central processing unit (CPU) in dotted line and a graphics processing unit (GPU) in dashed line when both CPU and GPU are functioning using example embodiments of the present invention on a second data set.
Figure 12:
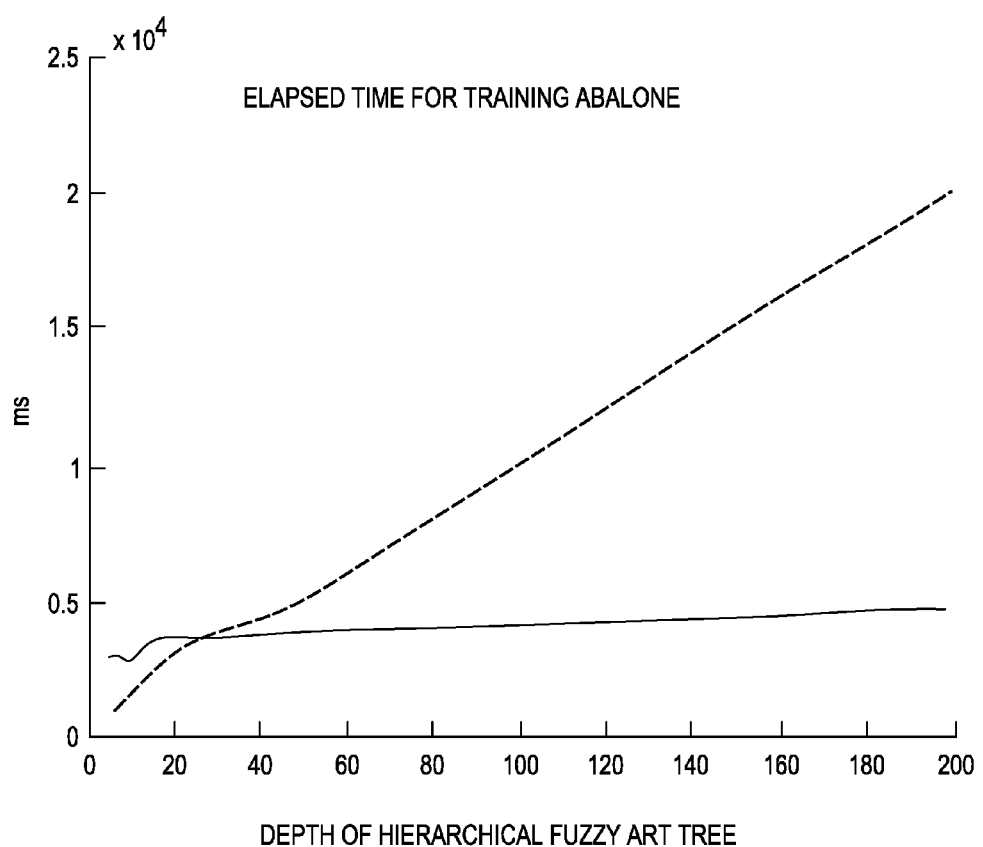
FIG. 12 is a graph showing elapsed time as a function of depth of the hierarchical ART tree for both a central processing unit (CPU) in dotted line and a graphics processing unit (GPU) in dashed line when both CPU and GPU are functioning using example embodiments of the present invention on a third data set.

FIGS. 10-12 each show the elapsed time measure on each platform. When the tree depth is low, the CPU running speed is faster as the algorithm was based on layer pipelining. But as the depth grows to meet a certain value, the performance of the GPU implementation exceeds that of the CPU application. The point where the GPU exceeds the CPU varies on each data set as shown in FIG. 13. The time comparison chart implies that the larger the dimension of the data is, the sooner the GPU surpasses the CPU. The maximum speed boost was by 1170% on 2d-10c data with 200 layers. The average performance improvement is 859.37%, 527.95%, 294.74% and 140.46% on 200, 100, 50 and 20 layers, respectively.

Figure 14:
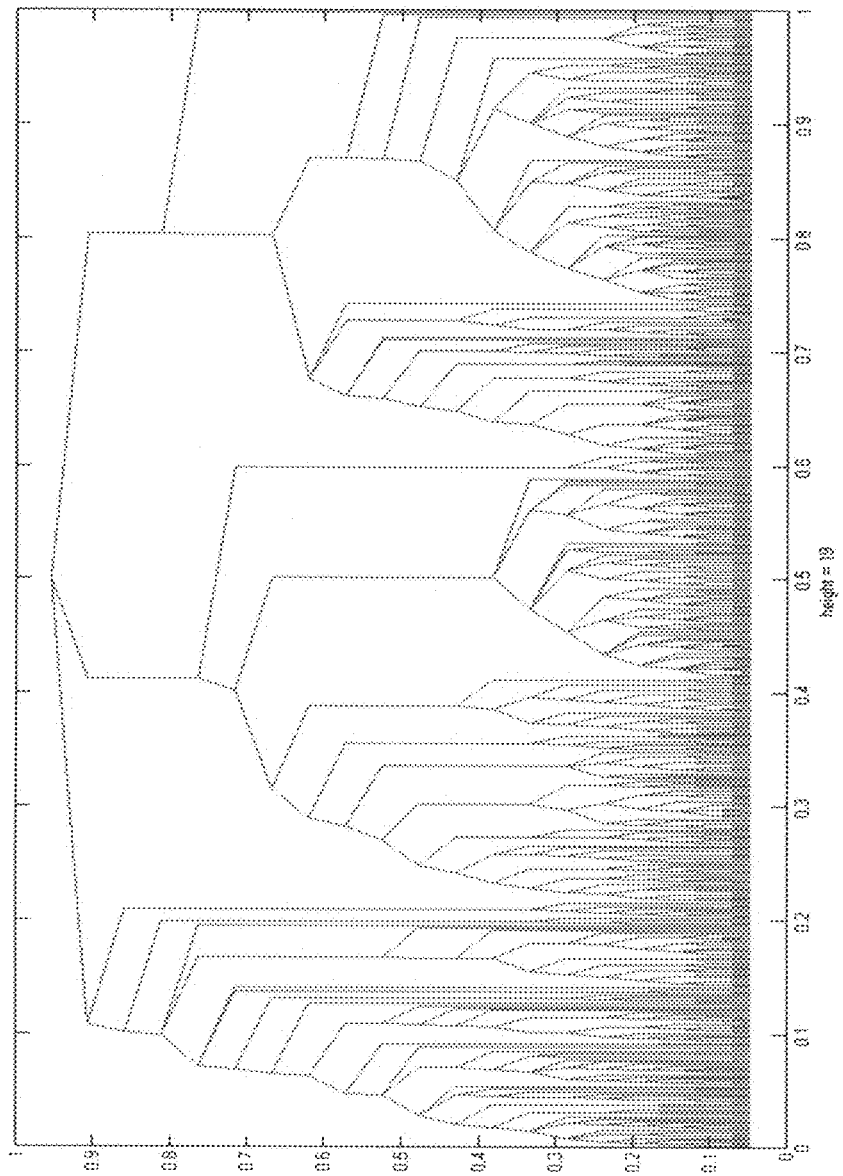
FIG. 14 is tree the illustrates how finely the samples can be fragmented in accordance with an example embodiment.

FIG. 14 illustrates a tree showing how data can be divided using the present methods and systems described herein. A large data set can be fed into the FIG. 2 system and can result in a plurality of clusters, here three clusters. Each of these clusters can be fed back into the FIG. 2 system which can further cluster and fragment the data of any individual cluster. As shown the leftmost cluster is divided into two more clusters at the next level. A leftmost cluster is then broken into two clusters. The leftmost cluster at that level is then divided into three clusters. Accordingly, FIG. 14 shows how finely the samples can be fragmented. The results also show that such deep clustering can be accomplished faster than CPU based algorithms. Hierarchical Fuzzy ART (HF-ART) on GPU can provide a notifiable speed improvement. It is also believed that hierarchical ART clustering in GPU processors is a significant improvement in processing high data loads and computational demands, such as in data mining and bioinformatics. Each of the paths shown in FIG. 14 can be executing on a different computing system. This lends to parallel processing of the data set.

This example can overcome the inflexibility of memory inside the kernel in the CUDA system. Inflexibility in this context may mean that the generation of dynamic arrays are limited only in the host (CPU) side. A further difficulty that may be overcome in this example is that typical tree structure algorithms implement pointers for both node creation and reference, which is inefficient to do in CUDA programming. The other is that each ART unit is trained as data are fed sequentially. GPU implementation can implement the hierarchical fuzzy ART of the present disclosure.

Figure 15:
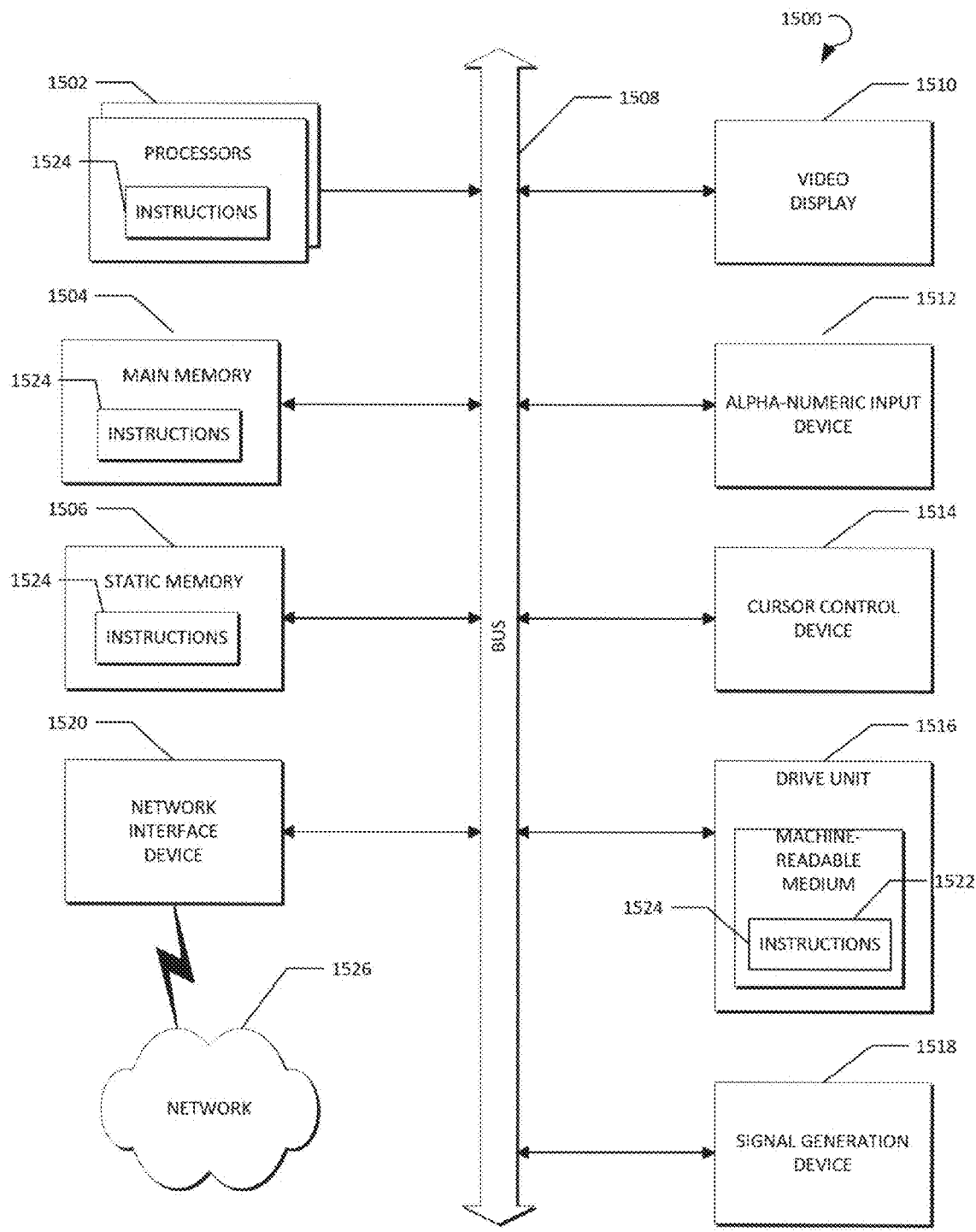
FIG. 15 is a schematic view of a computing system according to an example embodiment.

FIG. 15 shows a diagrammatic representation of machine in the example form of a computer system 1500 within which a set of instructions may be executed causing the machine to perform any one or more of the methods, processes, operations, applications, or methodologies discussed herein. The ART units or modules and layers described herein may include the functionality of at least one of the computing system 1500.

In an example embodiment, the computing machine operates as a standalone device or may be connected (e.g., networked) to other machines. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1500 includes a processor 1502 (e.g., a central processing unit (CPU) a graphics processing unit (GPU) or both), a main memory 1504 and a static memory 1506, which communicate with each other via a bus 1510. The computer system 1500 may further include a video display unit 1510 (e.g., a liquid crystal display (LCD), plasma display, or a cathode ray tube (CRT)). The computer system 1500 also includes an alphanumeric input device 1512 (e.g., a keyboard), a cursor control device 1514 (e.g., a mouse), a drive unit 1516, a signal generation device 1518 (e.g., a speaker) and a network interface device 1520.

The drive unit 1516 includes a machine-readable medium 1522 on which is stored one or more sets of instructions (e.g., software 1524) embodying any one or more of the methodologies or functions described herein. The software 1524 may also reside, completely or at least partially, within the main memory 1504 and/or within the processor 1502 during execution thereof by the computer system 1500, the main memory 1504 and the processor 1502 constituting machine-readable media.

The software 1524 may further be transmitted or received over a network 1526 via the network interface device 1520. While the machine-readable medium 1522 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies shown in the various embodiments of the present invention. The term "machine-readable medium" shall accordingly be taken to include, but not be limited to, solid-state memories and optical and magnetic media, and physical carrier constructs.

Portions of the present description may appear to refer to users, collaborators, managers, providers, etc. as individuals. However, in many embodiments these references refer to devices, such as computer devices (e.g., the FIG. 15 device), that can electronically communicate with other devices.

Certain systems, apparatus, applications or processes are described herein as including a number of modules or mechanisms. A module or a mechanism can be a unit of distinct functionality that can provide information to, and receive information from, other modules. Accordingly, the described modules may be regarded as being communicatively coupled. Modules may also initiate communication with input or output devices, and can operate on a resource (e.g., a collection of information). The modules be implemented as hardware circuitry, optical components, single or multi-processor circuits, memory circuits, software program modules and objects, firmware, and combinations thereof, as appropriate for particular implementations of various embodiments.

Aspects of the embodiments are operational with numerous other general purpose or special purpose computing environments or configurations can be used for a computing system. Examples of well known computing systems, environments, and/or configurations that may be suitable for use with the embodiments include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The communication systems and devices as described herein can be used with various communication standards to connect. Examples include the Internet, but can be any network capable of communicating data between systems. other communication standards include a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line. Communications network 22 may yet further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection.

Aspects of the embodiments may be implemented in the general context of computer-executable instructions, such as program modules, being executed by a computer. Generally, program modules include routines, programs, objects, components, data structures, etc. that perform particular tasks or implement particular abstract data types. Aspects of the embodiments may also be practiced in distributed computing environments where tasks are performed by remote processing devices that are linked through a communications network. In a distributed computing environment, program modules may be located in both local and remote computer storage media including memory storage devices.

Figure 16:
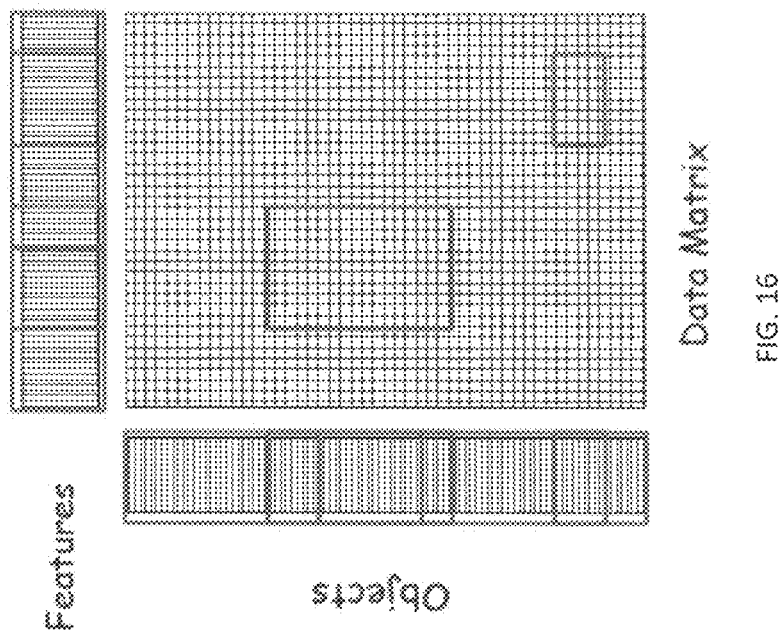
FIG. 16 is a data matrix on which the present structures and methods can act.

FIG. 16 shows a data matrix on which the presently described methods can act or which can be input into the presently described structures. The data matrix has dimensions of data in rows and columns. Select subspaces, here shown enclosed in boxes, can be input into the biclustering device, e.g., the device shown in FIG. 2 with the rows being input into the $ART_a$ and the rows input into $ART_b$. The output of the $ART_a$ is column cluster(s). The output of the $ART_b$ is row cluster(s). These resulting clusters can then be thought of as a new data matrix and sent back into the $ART_a$ and the $ART_b$ for hierarchical biclustering. The inter-ART module interrelates the certain column cluster(s) to certain row cluster(s).

Figure 17:
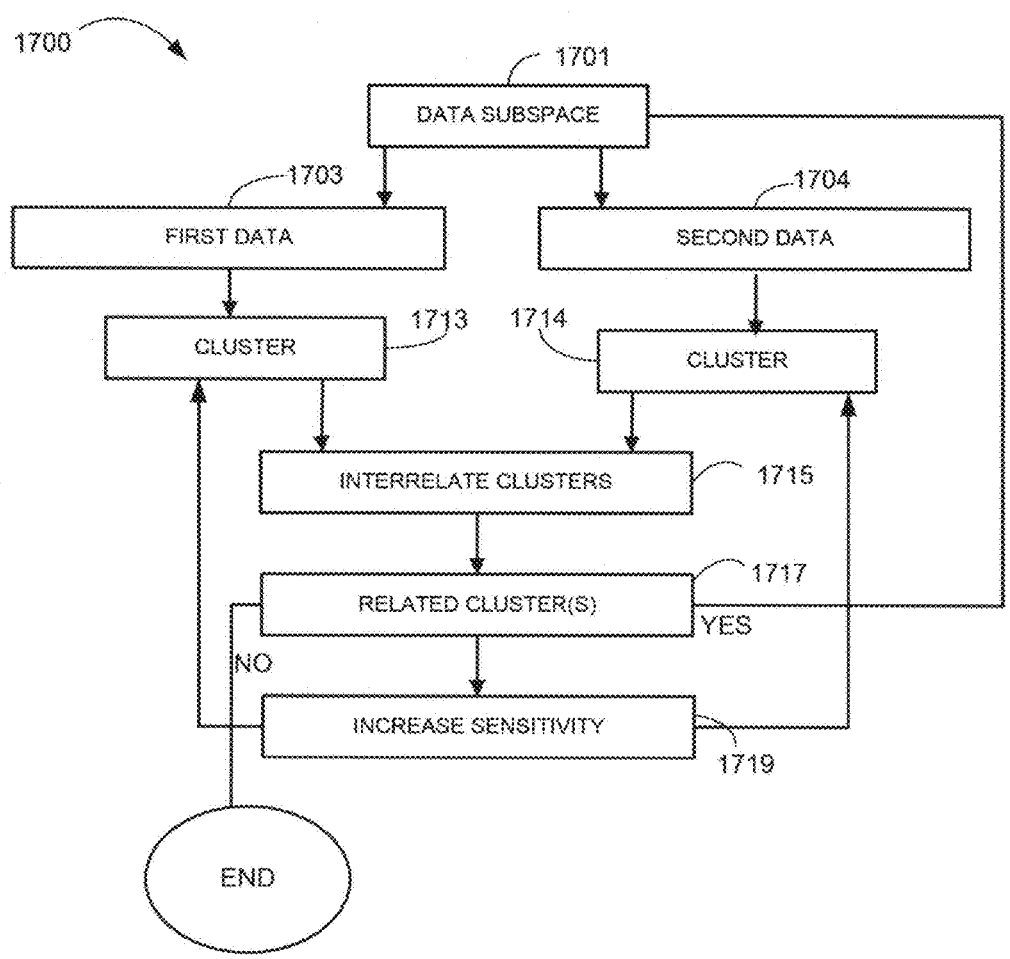
FIG. 17 is a flow chart of a process in accordance with an example embodiment.

FIG. 17 shows a hierarchical biclustering method 1700 for according to an example embodiment. At 1701, a data subspace from a data set is presented. In an example, the data may be the data matrix as shown in FIG. 16. In this example, the data subspace may be one of the two dimensional subspaces shown as rectangles, with a column dimension and a row dimension, as shown in FIG. 16. The data set is divided into a plurality of data dimensions to create first data and second data, 1703 and 1704. This first data 1703 and the second data 1704 do not have known labels or relationships. At 1713, the first data is clustered. At 1714, the second data is clustered. If data does not cluster, then the data is discarded. The resulting clusters from both clustering steps 1713 and 1714 are then interrelated at 1715 to form interrelated clusters 1717. If clusters do not interrelate then, those clusters may be discarded. If there are interrelated clusters, then the sensitivity of the clustering is increased at the clustering 1713, 1714. Each interrelated cluster at 1717 can be fed back into both first data 1703 and the second data 1704. The process can then repeat for this new data based on the cluster, which is a subset of the original data. This process may be repeated multiple times and may result in the tree structure of FIG. 16 or similar structure when repeated. Accordingly, the method 1700 results in a hierarchical biclustering of the original data set.

The present disclosure makes reference to a paper titled A GPU based Parallel Hierarchical Fuzzy ART Clustering, Proceedings of International Joint Conference on Neural Networks, San Jose, Calif., USA, Jul. 31-Aug. 5, 2011, authors Sejun Kim and Donald Wunsch, which is hereby incorporated by reference for any purpose.

Methods and systems for biclustering and hierarchical biclustering have been described. Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

The present methods and structures can provide unsupervised learning using biclustering that allow the device and methods to learn the data and the labels at the same time. The use of biclustering may speed up processing of the data set in which known correct clustering or relationships between the data are not known.

Biclustering performs simultaneous clustering on features and data automatically integrating feature selection to clustering without any prior information, so that the relations of clusters of unsupervised labels (for example, genes) and clusters of data (for example, samples or conditions) are established. However, typical approaches have NP-complete computational complexity, which raises a great challenge to computational methods for identifying such local relations. As described herein a neural-based classifier can be modified to perform biclustering in an efficient way. Experimental results on multiple human cancer data sets show that the algorithm can achieve clustering structures with higher qualities than or compared to those with other commonly used biclustering or clustering algorithms. The high speed of this algorithm may be a considerable advantage.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method for clustering information from a data set, comprising:
    creating first clusters of related data from a first subspace of unclustered data in the data set, wherein related data added to each one of the first clusters shares at least one attribute in the first subspace; and
    creating second clusters of related data from a second subspace of unclustered data in the data set, wherein adding the related data from the second subspace to one of the second clusters requires satisfying a vigilance parameter to ensure each one of the second clusters of related data shares at least one attribute in the second subspace; and
    providing feedback to increase the vigilance parameter if the related data from the second subspace added to the one of the second clusters does not share at least one attribute associated with one of the first clusters, wherein increasing the vigilance parameter forces the related data from the second subspace to be added to a new or different one of the second clusters.

2. The method of claim 1, comprising inputting the second clusters of related data into the creating first cluster and creating the second cluster, including but not limited to, iteratively.

3. The method of claim 2, wherein the first subspace of unclustered data and the second subspace of unclustered data are not known correct cluster data.

4. The method of claim 1, wherein the first subspace of unclustered data is gene data.

5. The method of claim 4, wherein the second subspace of unclustered data is sample data.

6. The method of claim 1, wherein the creating the first clusters is unsupervised and wherein the creating the second clusters is unsupervised.

7. The method of claim 6, wherein creating second clusters is unsupervised.

8. The method of claim 1, wherein creating second clusters is unsupervised.

9. The method of claim 1, wherein the method is repeatedly applied within the first clusters and the second clusters so generated, in order to obtain a hierarchical clustering.

10. A data interpretation system, comprising:
    a first module, implemented by one or more processors in the data interpretation system, to receive a first subspace of unclustered inputs from a data set and to produce first clusters based on a vigilance parameter maintained by the first module;
    one or more additional modules, implemented by the one or more processors in the data interpretation system, to receive one or more additional subspaces of unclustered inputs from the data set and to produce additional clusters; and
    a third module, implemented by the one or more processors in the data interpretation system, that provides feedback to the first module to increase the vigilance parameter of the first module if data of the first subspace of unclustered inputs added to one of the first clusters does not share an attribute with other data in one of the additional clusters, wherein increasing the vigilance parameter of the first module forces the data of the first subspace of unclustered inputs to be added to a new or a different one of the first clusters.

11. The system of claim 10, wherein the one or more additional modules receives additional subspaces of unclustered inputs from the data set without any feedback from the third module.

12. The system of claim 10, wherein the first module is an adaptive resonance theory device and wherein the one or more additional modules is an adaptive resonance theory device.

13. The system of claim 10, wherein any module of the first module, the one or more additional modules or the third module includes a graphical processing unit.

14. The system of claim 10, wherein the second subspace of unclustered inputs are not known correct cluster data.

15. A method for clustering information from a data set, comprising:
    utilizing a first adaptive resonance theory (ART) module to add unclustered data from a first subspace to a selected one of a first set of clusters, wherein the unclustered data from the first subspace added to the selected one of the first set of clusters shares at least one attribute in the first subspace with other data in the selected one of the first set of cluster;
    utilizing a second adaptive resonance theory (ART) module to add unclustered data from a second subspace to a selected one of a second set of clusters, wherein a vigilance parameter is utilized by the second ART module to ensure unclustered data from the second subspace added to the selected one of the second set of clusters shares at least one attribute in the second subspace with other data in the selected one of the second set of clusters; and
providing feedback to the second ART module to increase the vigilance parameter associated with the second ART module if the unclustered data from the second subspace does not share an attribute with other data in the selected one of the second set of clusters across one of the first set of clusters, wherein increasing the vigilance parameter results in the second ART module forcing the unclustered data from the second subspace added to a new or different one of the second set of clusters.

* * * * *